(12) United States Patent
Kang et al.

(10) Patent No.: US 11,987,817 B2
(45) Date of Patent: May 21, 2024

(54) METHOD OF MANUFACTURING CELL SPHEROID USING BIOINK

(71) Applicant: UNIST (ULSAN NATIONAL INSTITUTE OF SCIENCE AND TECHNOLOGY), Ulsan (KR)

(72) Inventors: Hyun Wook Kang, Ulsan (KR); Seug Gyu Jeon, Ulsan (KR); Jun Ho Heo, Ulsan (KR)

(73) Assignee: UNIST (ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 847 days.

(21) Appl. No.: 16/751,008

(22) Filed: Jan. 23, 2020

(65) Prior Publication Data
US 2020/0283736 A1 Sep. 10, 2020

(30) Foreign Application Priority Data
Mar. 6, 2019 (KR) .................. 10-2019-0025956

(51) Int. Cl.
| | |
|---|---|
| C12N 5/071 | (2010.01) |
| B29C 64/106 | (2017.01) |
| B29K 67/00 | (2006.01) |
| B33Y 10/00 | (2015.01) |
| B33Y 70/10 | (2020.01) |

(52) U.S. Cl.
CPC .......... *C12N 5/0697* (2013.01); *B29C 64/106* (2017.08); *B29K 2005/00* (2013.01); *B29K 2067/00* (2013.01); *B33Y 10/00* (2014.12); *B33Y 70/10* (2020.01); *C12N 2502/081* (2013.01); *C12N 2502/1323* (2013.01); *C12N 2502/14* (2013.01); *C12N 2502/22* (2013.01); *C12N 2502/28* (2013.01); *C12N 2513/00* (2013.01); *C12N 2533/54* (2013.01)

(58) Field of Classification Search
CPC ............. C12N 5/0697; C12N 2513/00; B29C 64/106; B33Y 10/00; B33Y 70/10; B29K 2005/00; B29K 2067/00
See application file for complete search history.

(56) References Cited

U.S. PATENT DOCUMENTS

| | | | |
|---|---|---|---|
| 9,867,781 B2 * | 1/2018 | Anderson | A61K 45/06 |
| 2013/0302885 A1 * | 11/2013 | Lai | C12N 5/0621 435/325 |
| 2017/0216498 A1 * | 8/2017 | Kang | A61L 27/20 |
| 2018/0230423 A1 * | 8/2018 | O'Mahony | C12M 21/08 |
| 2018/0280578 A1 * | 10/2018 | Hwang | A61L 27/222 |
| 2018/0348637 A1 * | 12/2018 | Hribar | B33Y 10/00 |

FOREIGN PATENT DOCUMENTS

| | | | |
|---|---|---|---|
| KR | 10-1743231 B1 | 6/2017 | |
| KR | 10-2018-0032597 A | 3/2018 | |
| WO | WO-2015027086 A1 * | 2/2015 | ............. A61L 27/20 |
| WO | WO-2017091662 A1 * | 6/2017 | ............. C12M 25/10 |
| WO | WO-2018005477 A1 * | 4/2018 | ............. A61K 35/35 |
| WO | WO-2018073235 A1 * | 4/2018 | ............. A61K 35/35 |

OTHER PUBLICATIONS

Mironov, Vladimir, et al. "Organ printing: tissue spheroids as building blocks." Biomaterials 30.12 (2009): 2164-2174. (Year: 2009).*
Khalil, Saif, and Wei Sun. "Bioprinting endothelial cells with alginate for 3D tissue constructs." Journal of biomechanical engineering 131.11 (2009). (Year: 2009).*
Xu, Changxue, Yong Huang, and Roger R. Markwald. "Vertical and horizontal fabrication of alginate-based vascular-like constructs using inkjetting." 2012 International Solid Freeform Fabrication Symposium. University of Texas at Austin, 2012. (Year: 2012).*
Cao, N., X. B. Chen, and D. J. Schreyer. "Influence of calcium ions on cell survival and proliferation in the context of an alginate hydrogel, ISRN Chem." (2012). (Year: 2012).*
Xu, Changxue, et al. "Freeform vertical and horizontal fabrication of alginate-based vascular-like tubular constructs using inkjetting." Journal of Manufacturing Science and Engineering 136.6 (2014). (Year: 2014).*
Jia, J., Richards, D. J., Pollard, S., Tan, Y., Rodriguez, J., Visconti, R. P., . . . & Mei, Y. (2014). Engineering alginate as bioink for bioprinting. Acta biomaterialia, 10(10), 4323-4331. (Year: 2014).*
Therese Andersen et al, "3D Cell Culture in Alginate Hydrogels" (Mar. 24, 2015) Microarrays, vol. 4, No. 2, Mar. 24, 2015, pp. 133-161 (Year: 2015).*
Zhu, Benwei, and Heng Yin. "Alginate lyase: Review of major sources and classification, properties, structure-function analysis and applications." Bioengineered 6.3 (2015): 125-131. (Year: 2015).*
Jia, Weitao, et al. "Direct 3D bioprinting of perfusable vascular constructs using a blend bioink." (2016) Biomaterials 106: 58-68. (Year: 2016).*
Dubbin, Karen, et al. "Dual-stage crosslinking of a gel-phase bioink improves cell viability and homogeneity for 3D bioprinting." Advanced healthcare materials 5.19 (2016): 2488-2492. (Year: 2016).*

(Continued)

*Primary Examiner* — Arthur S Leonard
*Assistant Examiner* — Josephine M Gonzales
(74) *Attorney, Agent, or Firm* — Studebaker & Brackett PC

(57) ABSTRACT

Disclosed is a process of manufacturing cell spheroids using a bioink. More particularly, provided is a method of manufacturing a cell spheroid, the method including extruding a first bioink including an alginate; extruding a second bioink including cells into the extruded first bioink; adding a calcium chloride (CaCl2) solution to the alginate included in the first bioink; and dissolving the second bioink, present in the first bioink, in a cell culture medium to form a cell spheroid from the cells.

15 Claims, 10 Drawing Sheets

(56) References Cited

OTHER PUBLICATIONS

Ginn, Brian Patrick. The Development of Hydrogel Microfiber Scaffolds for Peripheral Nerve Repair. 2017, Diss. Johns Hopkins University (Year: 2017).*

Moldovan, Nicanor I., Narutoshi Hibino, and Koichi Nakayama. "Principles of the Kenzan method for robotic cell spheroid-based three-dimensional bioprinting." Tissue Engineering Part B: Reviews 23.3 (2017): 237-244. (Year: 2017).*

Peng, Chune, et al. "A novel bifunctional endolytic alginate lyase with variable alginate-degrading modes and versatile monosaccharide-producing properties." Frontiers in Microbiology 9 (2018): 167. (Year: 2018).*

Reakasame, Supachai, and Aldo R. Boccaccini. "Oxidized alginate-based hydrogels for tissue engineering applications: a review." Biomacromolecules 19.1 (2018): 3-21. (Year: 2018).*

Tarassoli, S. P., et al. "Candidate bioinks for 3D bioprinting soft tissue." 3D Bioprinting for Reconstructive Surgery. Woodhead Publishing, 2018. 145-172. (Year: 2018).*

Kundu, Joydip, et al. "An additive manufacturing-based PCL-alginate-chondrocyte bioprinted scaffold for cartilage tissue engineering." Journal of tissue engineering and regenerative medicine 9.11: 1286-1297. (Year: 2015).*

H. W. Kang; "One-step Fabrication of the Transplantable Construction Containing B-cell Spheroids by 3D Bioprinting Process"; Korean Society of Precision Engineering; The Fall 2018 collection of learned papers; May 2018; p. 829.

S. G. Jeon et al; "Development of the Bioprinting Process for 3D Micro-Positioning with In-Situ formation of Cell Spheroids"; Korean Society of Precision Engineering; The Fall 2018 collection of learned papers; Oct. 2018; p. 96.

An Office Action mailed by the Korean Intellectual Property Office on Apr. 17, 2020, which corresponds to Korean Patent Application No. 10-2019-0025956 and is related to U.S. Appl. No. 16/751,008.

A Notice of Allowance mailed by the Korean Intellectual Property Office on Aug. 25, 2020, which corresponds to Korean Patent Application No. 10-2019-0025956 and is related to U.S. Appl. No. 16/751,008.

* cited by examiner

Fig. 4A
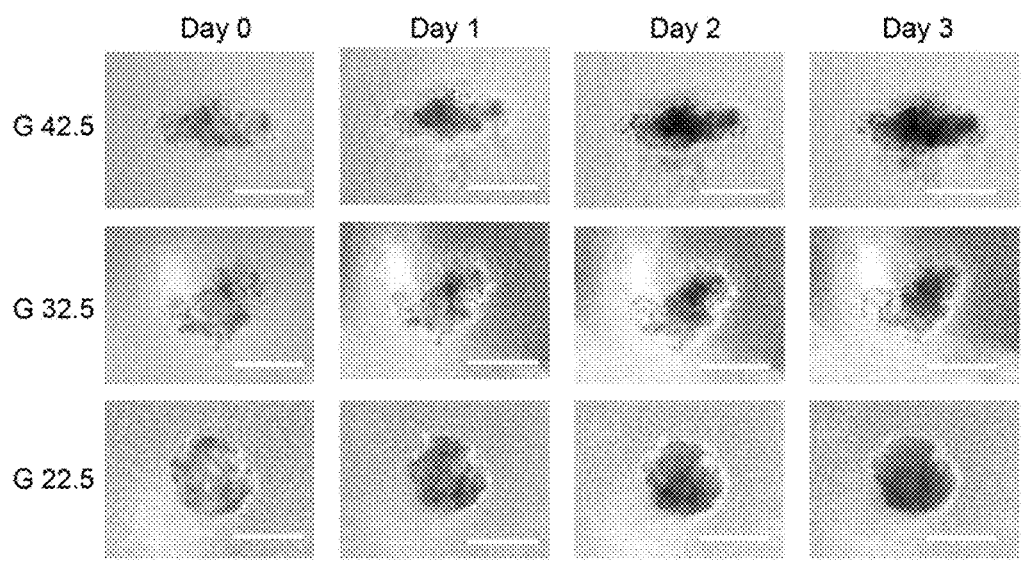
Fig. 4B
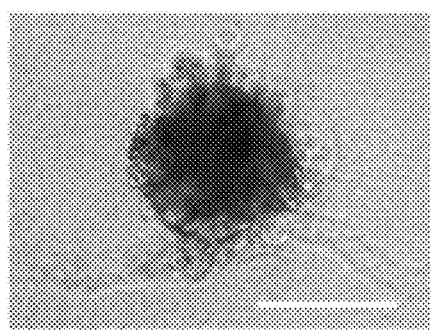
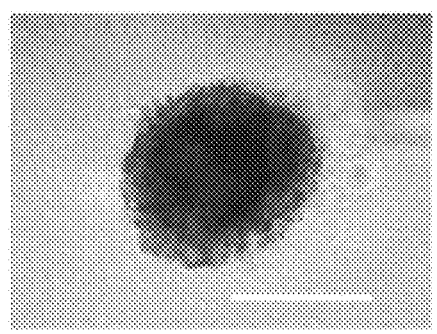

Fig. 7A
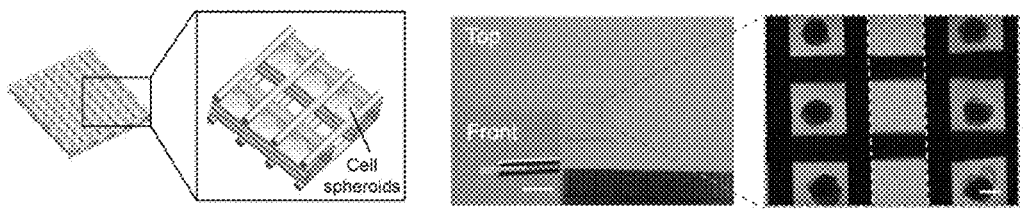
Fig. 7B
Multi-cellular spheroids patterned
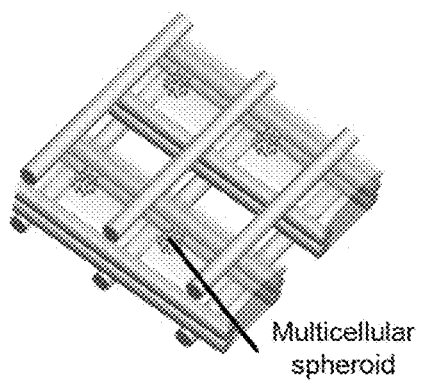
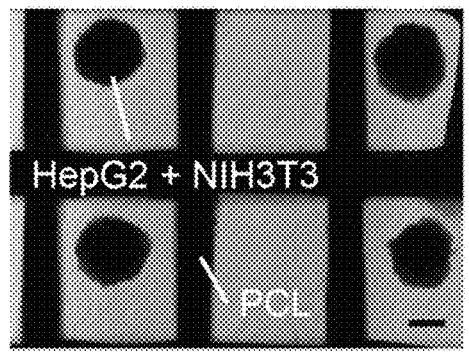
Multi-type spheroids patterned
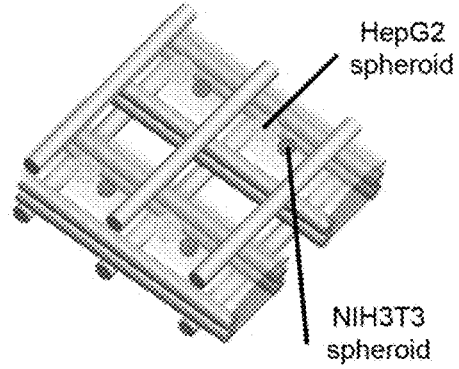
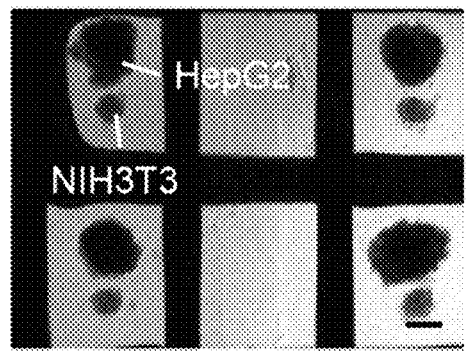

METHOD OF MANUFACTURING CELL SPHEROID USING BIOINK

CROSS-REFERENCE TO RELATED APPLICATION

This application claims priority to and the benefit of Korean Patent Application No. 10-2019-0025956, filed on Mar. 6, 2019, the disclosure of which is incorporated herein by reference in its entirety.

BACKGROUND

1. Field of the Invention

The present disclosure relates to a method of manufacturing a cell spheroid, and more particularly, to a method of manufacturing cell spheroids using a bioink.

2. Discussion of Related Art

Conventionally, cell spheroids have been manufactured by injecting cells into microwells to which cells cannot be attached. In this case, complicated and long micromachining processes such as photolithography and soft-lithography are required to manufacture microwells.

In addition, in the case of existing methods, there are limitations in adjusting the sizes of cell spheroids, and it is not easy to harvest manufactured cell spheroids. Further, cell spheroids have been manufactured by culturing cells in hanging drops or culturing cells on a surface to which the cells cannot be attached. However, these methods are inconvenient for exchanging a cell culture medium and cells may be lost during exchange of the cell culture medium.

Accordingly, technologies wherein cell spheroids are separately manufactured and then bio-printed to manufacture macro artificial tissues were developed. As a representative example, agarose gel rods were first printed, and then a bioink mixed with cell spheroids was printed between the agarose gel rods.

In addition, a technology of inserting cell spheroids into a micro-needle to pattern the cell spheroids using computer imaging and robotics technology has been developed. However, in the case of this method, it is required to separately manufacture cell spheroids, and complex computer imaging and robotics systems should be used. In addition, there is a problem that the accuracy of patterns among cell spheroids and various types of cells is inferior.

RELATED ART DOCUMENT

Patent Document (Patent Document 1)[Patent Document 1] Korean Patent No. 10-1743231

SUMMARY OF THE INVENTION

Therefore, the present disclosure has been made in view of the above problems, and it is an objective of the present disclosure to provide a method of manufacturing cell spheroids using a bioink.

It is another objective of the present disclosure to provide a method of inducing the formation of a cell spheroid at a site (in-situ) into which a bioink is extruded through a process of extruding the bioink, including cells, into a hydrogel. It is still another objective of the present disclosure to provide a method of extruding a second bioink including dispersed single cells into a first bioink composed of a hydrogel matrix using a needle nozzle to provide an environment in which cells can form a spheroid.

It is yet another objective of the present disclosure to provide a process of controlling the sizes of cell spheroids while adjusting an extrusion amount of the second bioink including cells.

It is yet another objective of the present disclosure to provide a process of controlling the position of cell spheroid to be formed by controlling a printing path.

It is yet another objective of the present disclosure to provide a complex three-dimensional structure formed by patterning cell spheroids on a hydrogel through a hybrid bioprinting process.

It is yet another objective of the present disclosure to provide a process of patterning with multi-cellular spheroids or multi-spheroids using a bioink including multi-type cells.

In accordance with the present disclosure, the above and other objectives can be accomplished by the provision of a method of manufacturing a cell spheroid, the method including: extruding a first bioink including an alginate; extruding a second bioink including cells into the extruded first bioink; adding a calcium chloride (CaCl2) solution to the alginate included in the first bioink; and dissolving the second bioink, present in the first bioink, in a cell culture medium to form a cell spheroid from the cells.

In an embodiment, the method may further include extruding polycaprolactone (PCL) to form a first PCL structure and a second PCL structure, before the extruding of the first bioink.

In an embodiment, in the extruding of the first bioink, the first bioink including an alginate may be extruded between the formed first and second PCL structures.

In an embodiment, in the extruding of the first bioink, the first bioink including an alginate may be extruded onto a previously prepared plate.

In an embodiment, the first bioink may include hyaluronic acid, gelatin, and the alginate.

In an embodiment, the second bioink may include hyaluronic acid, gelatin, calcium chloride, and the cells In an embodiment, in the extruding of the second bioink, the second bioink may be spherically extruded according to at least one of a concentration of gelatin included in the first bioink and a concentration of gelatin included in the second bioink.

In an embodiment, the dissolving may include dissolving hyaluronic acid and gelatin, included in the second bioink in the first bioink, in the cell culture medium; and culturing the cells, included in the second bioink, in the cell culture medium for a predetermined time to form the cell spheroid from the cells.

In an embodiment, the extruding of the second bioink may include spherically extruding the second bioink, including cells, in the first bioink through a nozzle.

In an embodiment, a size of the formed cell spheroid may be determined according to at least one of an extrusion time and extrusion speed of the second bioink.

In an embodiment, a size of the formed cell spheroid may be determined according to a concentration of cells included in the second bioink.

In an embodiment, the spacing between the formed cell spheroids may be determined according to an extrusion path of the second bioink.

In an embodiment, the method may further include removing a matrix of the first bioink to extract the cell spheroid, after the dissolving.

In an embodiment, the method may further include adding an alginate lyase to the first bioink to remove the alginate from the first bioink and extract the cell spheroid.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which:

FIG. 4A illustrates the shapes of cell spheroids, dependent upon the concentration of gelatin included in a first bioink according to an embodiment of the present disclosure;

FIG. 4B illustrates the shapes of cell spheroids, dependent upon the types of cells included in a second bioink according to an embodiment of the present disclosure;

FIGS. 7A and 7B illustrate three-dimensional sheet structures formed by patterning cell spheroids according to an embodiment of the present disclosure;

DETAILED DESCRIPTION OF EXEMPLARY EMBODIMENTS

The terms such as "first" and "second" are used only for the purpose of distinguishing one constituent element from another constituent element. That is, the constituent elements are not limited by the terms.

Components, features, and steps that are referred to herein as being "comprised" mean that such components, features, and steps are present and are not intended to exclude one or more other components, features, steps, and equivalents thereof.

As used herein, the singular forms are intended to include the plural forms as well, unless the context clearly indicates otherwise. It will be further understood that components, etc., used in this specification do not preclude the presence or addition of one or more other components.

Unless otherwise defined, all terms (including technical and scientific terms) used herein have the same meaning as commonly understood by one of ordinary skill in the art to which this inventive concept belongs.

It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, a process of manufacturing cell spheroids using a bioink according to an embodiment of the present disclosure is described in detail with reference to the accompanying drawings.

Figure 1:
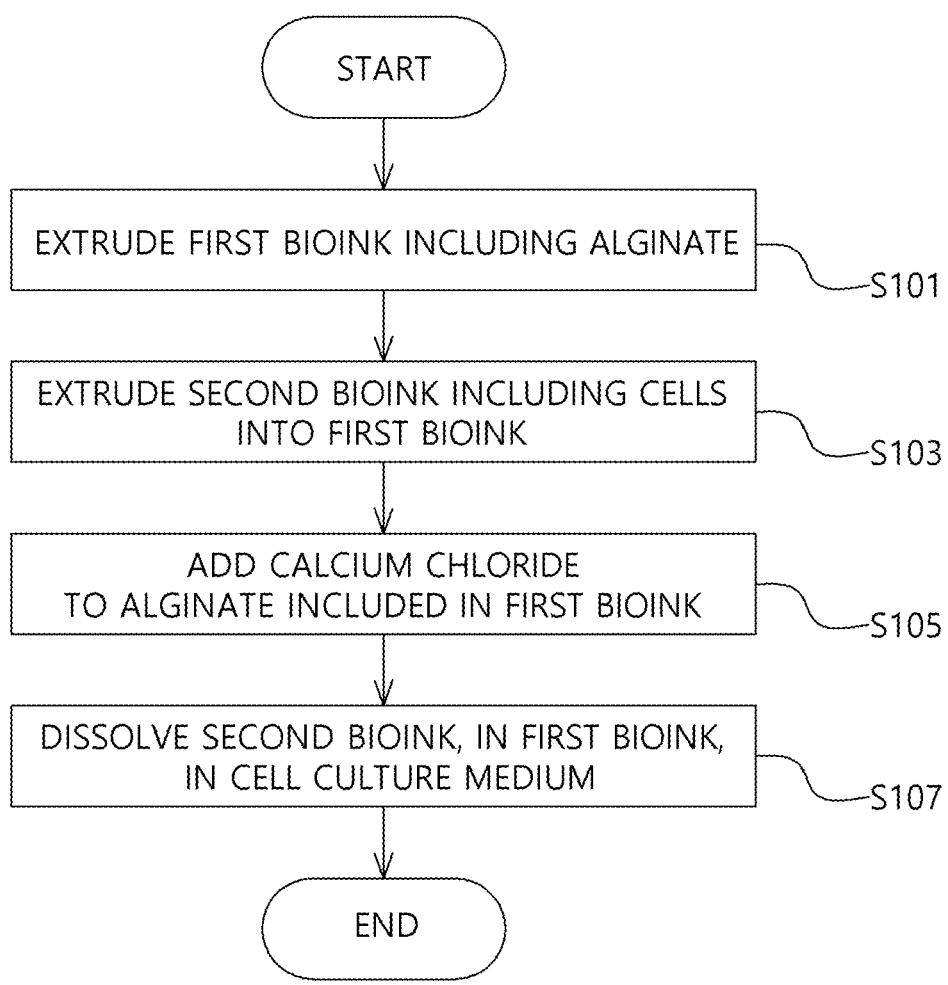
FIG. 1 illustrates a process of manufacturing cell spheroids according to an embodiment of the present disclosure.

FIG. 1 illustrates a method of manufacturing cell spheroids according to an embodiment of the present disclosure.

Referring to FIG. 1, S101 is a step of extruding a first bioink including an alginate. In an embodiment, before S101, a step of extruding polycaprolactone (PCL) to form a first PCL structure and a second PCL structure may be further included. In an embodiment, the first bioink including an alginate may be extruded between the formed first PCL structure and second PCL structure.

In an embodiment, the first bioink including an alginate may be extruded onto a previously prepared plate.

Here, the first bioink is composed of a substrate excluding cells and may be referred to as a matrix bioink, a substrate bioink, or various terms used in the equivalent sense.

S103 is a step of extruding a second bioink including cells into the extruded first bioink. In an embodiment, the first bioink may include hyaluronic acid, gelatin, and an alginate. In an embodiment, the second bioink may be spherically extruded according to at least one of the concentration of gelatin included in the first bioink and the concentration of gelatin included in the second bioink. In an embodiment, the second bioink may include hyaluronic acid, gelatin, calcium chloride, and cells. In an embodiment, the second bioink may be spherically extruded through a nozzle. For example, the nozzle may include a needle nozzle, but the type of nozzle is not specifically limited.

Here, the second bioink may include dispersed cells and may be referred to as a sacrificial bioink, a cell bioink or various terms used in the equivalent sense.

S105 is a step of adding a calcium chloride (CaCl2) solution to the alginate included in the first bioink. In an embodiment, calcium chloride in the calcium chloride solution may be crosslinked with the alginate.

S107 is a step of dissolving the second bioink, which is inside the first bioink, in a cell culture medium to form a cell spheroid from the cells. In an embodiment, hyaluronic acid and gelatin included in the second bioink inside the first bioink are dissolved in a cell culture medium, and then the cells included in the second bioink are cultured in the cell culture medium for a predetermined time, thereby forming a cell spheroid from the cells.

In an embodiment, the size of a cell spheroid to be formed may be determined according to at least one of a extrude time and extrude speed of the second bioink. In an embodiment, the size of a cell spheroid to be formed may be determined according to the concentration of cells included in the second bioink. In an embodiment, the spacing between cell spheroids to be formed may be determined according to an extrusion path of the second bioink.

Figure 2:
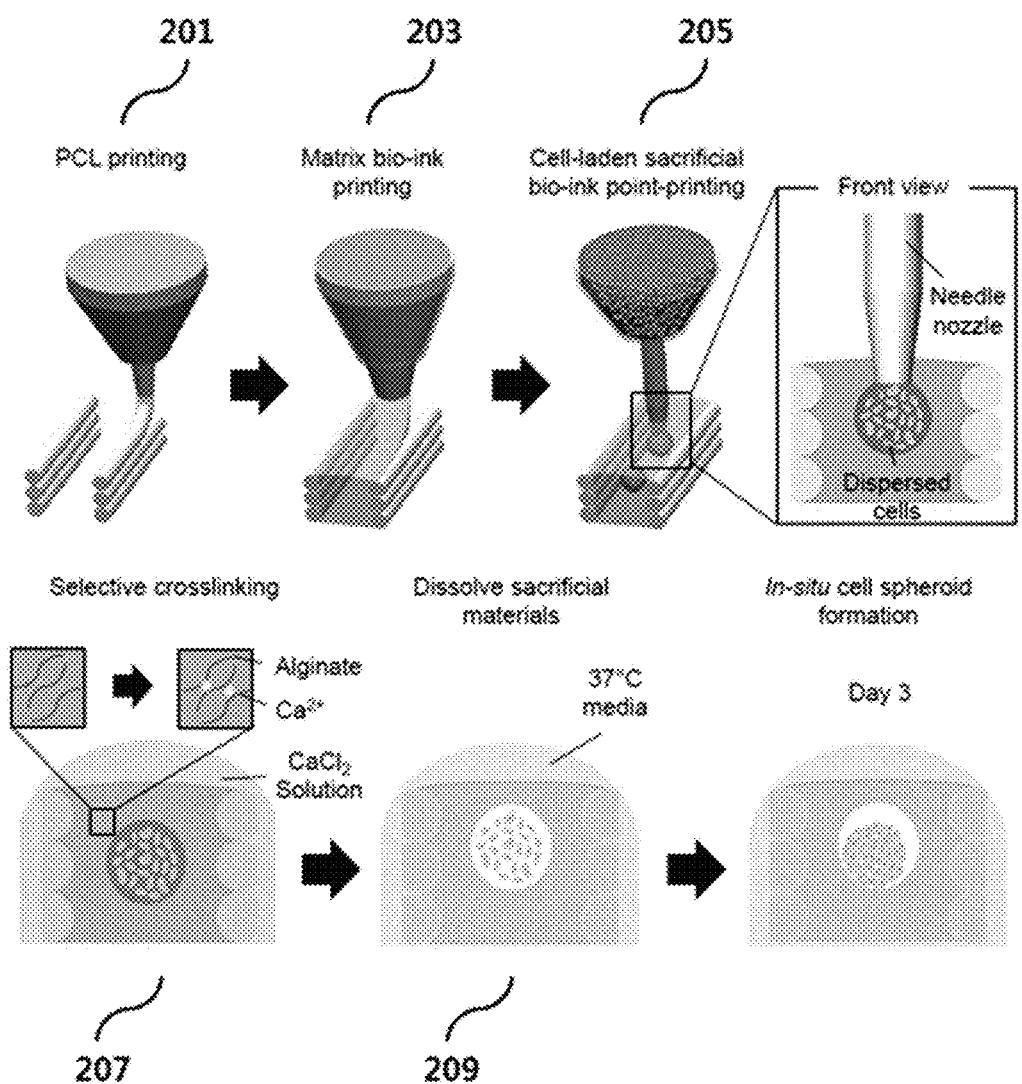
FIG. 2 illustrates a method of manufacturing cell spheroids according to an embodiment of the present disclosure.

FIG. 2 illustrates a method of manufacturing cell spheroids according to an embodiment of the present disclosure.

Referring to FIG. 2, in a PCL printing process (201), polycaprolactone (PCL) may be extruded to form PCL structures.

In a first bioink printing process (203), the first bioink may be extruded between the previously extruded PCL structures. In this case, the first bioink may be extruded between the PCL structures to form a matrix. In an embodiment, when the PCL printing process (201) is omitted, the first bioink may be directly extruded onto a previously prepared plate.

In a second bioink printing process (205), the second bioink (sacrificial bio-ink) including cells may be spherically extruded into the matrix of the first bioink using a needle nozzle. In this case, the second bioink may include calcium chloride (CaCl2). Due to crosslinking of the calcium chloride, the second bioink may be prevented from dispersing when injected into the matrix of the first bioink.

In a crosslinking process (207), a calcium chloride (CaCl2) solution may be additionally added to selectively crosslink with the alginate included in the first bioink. Accordingly, a spherical space formed by the second bioink may be maintained.

In a dissolution process (209), the sacrificial material included in the second bioink may be dissolved in a cell culture medium at a predetermined temperature. The predetermined temperature may be 35□ to 39□. In this case, the sacrificial material may include hyaluronic acid and gelatin. Next, due to an alginate-surrounding environment wherein cell attachment sites are not present in a space from which the sacrificial material of the second bioink is removed, cells may form spheroids after a certain time elapses. The certain time may be 2 to 4 days. That is, cells present in the second bioink are cultured in a cell culture medium, thereby forming cell spheroids.

In an embodiment, the first bioink used in the manufacturing process of the present disclosure may include at least one of hyaluronic acid, gelatin, and an alginate. In addition, the second bioink may include at least one of hyaluronic acid, gelatin, and calcium chloride.

In this case, each of the first bioink and the second bioink may include hyaluronic acid for uniform mixing of cells. In addition, each of the first bioink and the second bioink may include gelatin that is reversibly crosslinked dependent upon temperature. Accordingly, viscosity and printing ability may be controlled during printing.

The first bioink may include an alginate for selective crosslinking. The second bioink may include an alginate crosslinker, calcium chloride (CaCl2), for preventing dispersion when injected into the matrix of the first bioink.

In various embodiments of the present disclosure, each process shown in FIG. 1 is not essential, so some of the processes shown in FIG. 1 may be omitted and other processes may be added.

In various embodiments of the present disclosure, a bioprinter used in the manufacturing process of the present disclosure may include at least one printing module, a pneumatic dispenser for PCL extrusion, a mechanical dispenser for bioink extrusion, an enclosure for controlling the temperature and humidity of a space in which a printing process is performed, and a control module for generating a printing code through printing path generation software to control the manufacturing process of the present disclosure. In an embodiment, the temperature of a printing space may be constantly maintained for viscosity control with gelatin.

Figure 3A:
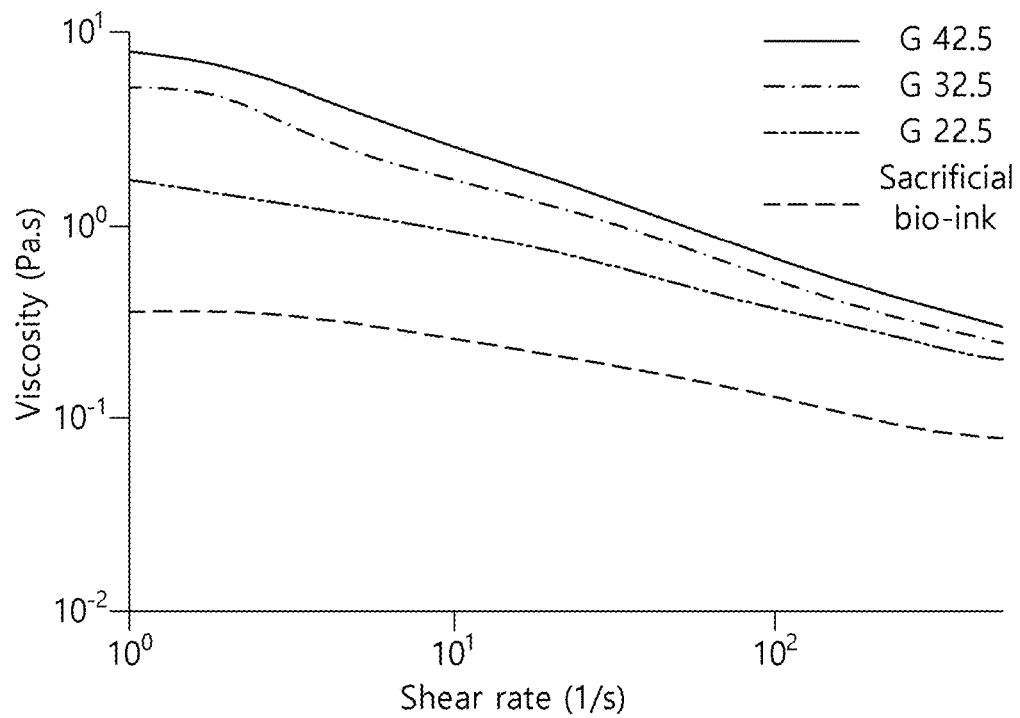
FIG. 3A illustrates a viscosity graph dependent upon the concentration of gelatin included in a first bioink according to an embodiment of the present disclosure.

FIG. 3A illustrates a viscosity graph dependent upon the concentration of gelatin included in a first bioink according to an embodiment of the present disclosure.

Referring to FIG. 3A, a viscosity change in the first bioink dependent upon the concentration of gelatin included in the first bioink was observed. The concentration of gelatin included in the first bioink was respectively adjusted to 42.5, 32.5, 22.5 mg/ml (denoted as G42.5, G32.5, and G22.5 in FIG. 3A), and the viscosities of the first bioink and the second bioink were compared. Here, it was confirmed that the viscosity of the first bioink increased with an increasing concentration of gelatin, and a viscosity difference between the first bioink and the second bioink was smallest at G22.5.

Figure 3B:
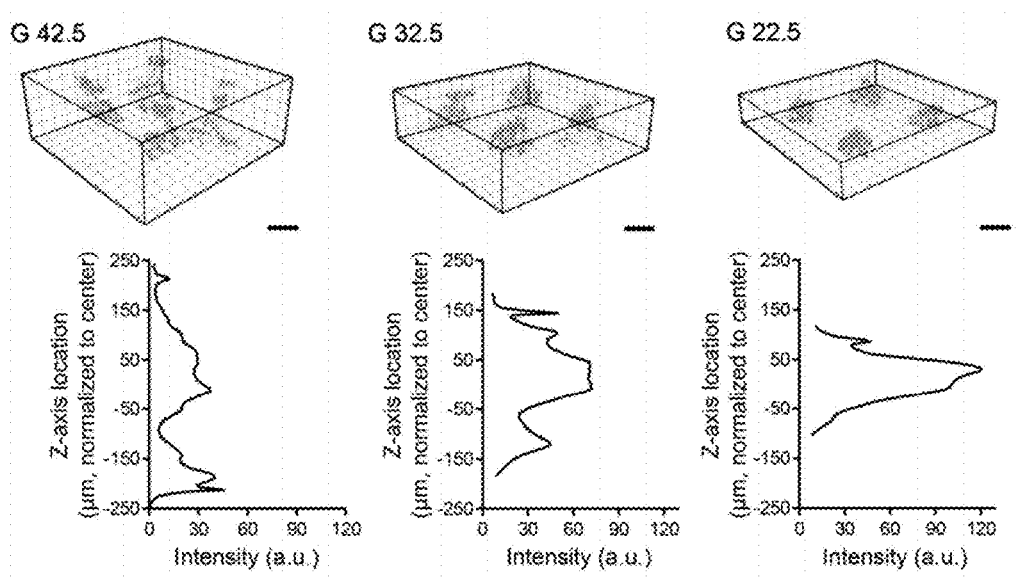
FIG. 3B illustrates the distribution and intensity of fluorescent beads included in a second bioink, dependent upon the concentration of gelatin included in a first bioink according to an embodiment of the present disclosure.

FIG. 3B illustrates the distribution and intensity of fluorescent beads included in a second bioink, dependent upon the concentration of gelatin included in a first bioink according to an embodiment of the present disclosure.

Referring to FIG. 3B, the concentration of gelatin included in the first bioink was respectively adjusted to G42.5, G32.5, and G22.5, and second bioinks including red fluorescent beads, instead of cells, were extruded.

In this case, it was confirmed that, when the concentration of gelatin in the first bioink was adjusted to 22.5 mg/ml, the second bioink was extruded in the shape of a relatively dense sphere. In addition, referring to the graphs normalized with respect to the center (scale bar: 200), an intensity distribution of fluorescent beads along the Z axis can be confirmed. That is, it was confirmed that the intensity was highest in the center of fluorescent beads.

FIG. 4A illustrates the shapes of cell spheroids, dependent upon the concentration of gelatin included in a first bioink according to an embodiment of the present disclosure.

Referring to FIG. 4A, the shapes of cell spheroids dependent upon the concentration of gelatin included in the first bioink were compared (scale bar: 200).

As in the fluorescent bead experiments, it was confirmed that, in the case in which HEK2 cells (liver carcinoma cells) were included in the second bioink, cells were extruded in the most spherical shape when the concentration of gelatin included in the first bioink was G22.5, and cell spheroids were formed on day 3 of culture.

FIG. 4B illustrates the shapes of cell spheroids, dependent upon the types of cells included in a second bioink according to an embodiment of the present disclosure.

Referring to FIG. 4B, other cell types were applied to the manufacturing process of the present disclosure, and the cell types were confirmed as forming cell spheroids (scale bar: 200). A PC12 cell line (neuronal like cell) having similar characteristics to nerve cells and a Min6 cell line having characteristics of pancreatic cells (pancreatic 13-cells) were applied to the manufacturing process of the present disclosure to manufacture cell spheroids. As a result, it was confirmed that the manufacturing process of the present disclosure may be applied to various cell types such as nerve cells to manufacture cell spheroids.

Figure 4C:
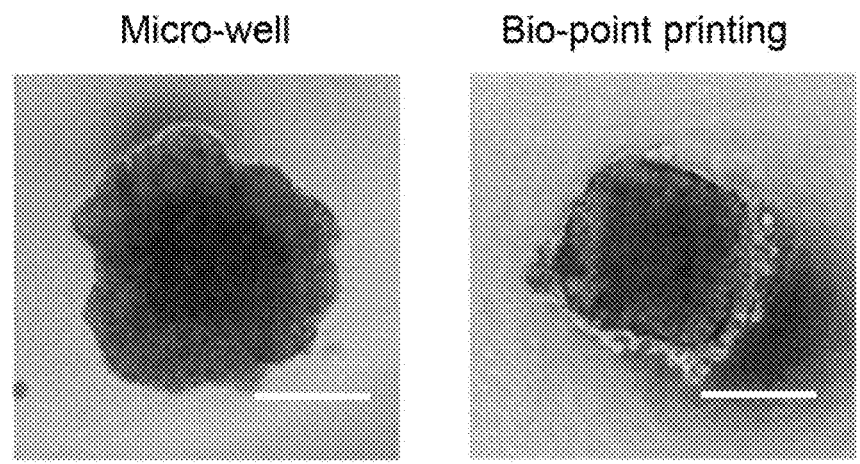
FIG. 4C is a view comparing a cell spheroid manufactured by a process according to an embodiment of the present disclosure with a cell spheroid manufactured by a conventional method.

FIG. 4C is a view comparing a cell spheroid manufactured by a process according to an embodiment of the present disclosure with a cell spheroid manufactured by a conventional method.

Referring to FIG. 4C, cell spheroids manufactured using microwells according to a conventional method and cell spheroids manufactured according to the manufacturing process of the present disclosure were harvested, and the shapes of the cell spheroids were compared (scale bar: 200). As a result, it was confirmed that the manufacturing process of the present disclosure enables cell spheroids to be manufactured in a similar shape as in a conventional method.

In this case, the cell spheroids according to an embodiment of the present disclosure may be harvested or extracted by removing the matrix of the first bioink. For example, an alginate lyase may be added within a range of about 2 U/ml to 4 U/ml to the first bioink to decompose the alginate in the first bioink and the cells may be cultured at 37□ for about 30 minutes to 1 hour to remove the matrix and harvest the cell spheroids.

Figure 4D:
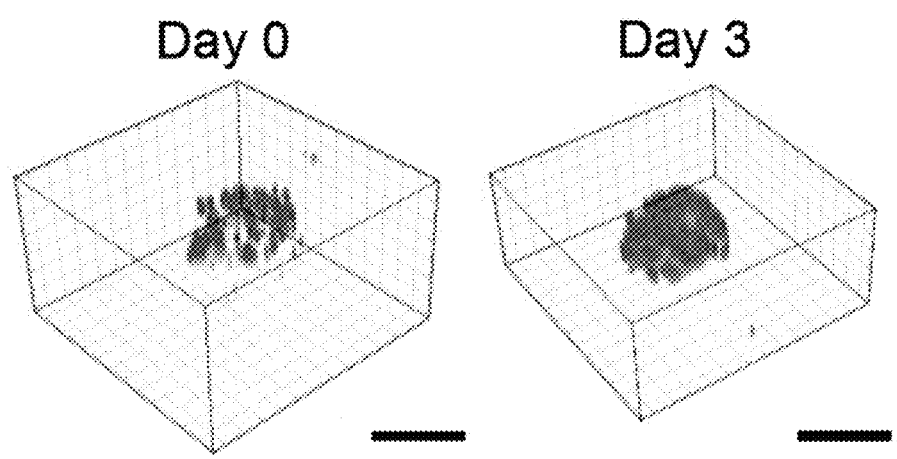
FIG. 4D illustrates incubation time-dependent cell spheroid shapes according to an embodiment of the present disclosure.

FIG. 4D illustrates incubation time-dependent cell spheroid shapes according to an embodiment of the present disclosure.

Referring to FIG. 4D, confocal microscope images of a cell spheroid manufactured according to the manufacturing process of the present disclosure were observed. In this case, it was confirmed that cells dispersed immediately after printing (Day 0) formed a three-dimensional cell spheroid on day 3 of culture.

Figure 5A:
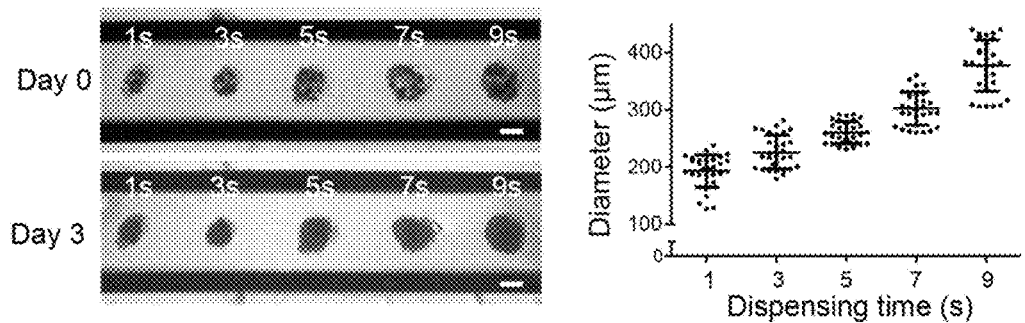
FIG. 5A illustrates cell spheroid sizes dependent upon an injection time of a second bioink according to an embodiment of the present disclosure.

FIG. 5A illustrates cell spheroid sizes dependent upon an extrusion time of a second bioink according to an embodiment of the present disclosure.

Referring to FIG. 5A, it was confirmed that the size of cell spheroid depended upon an extrusion time of the second bioink. It was confirmed that, when an extrusion time of the second bioink including cells was increased from 1 second to 9 seconds at intervals of 2 seconds, a cell extrusion amount increased and much larger cell spheroids were formed on day 3 of culture (scale bar: 200). In addition, it can be confirmed from a dot plot graph that the size of spheroid increases with an increasing extrusion time of the second bioink.

Figure 5B:
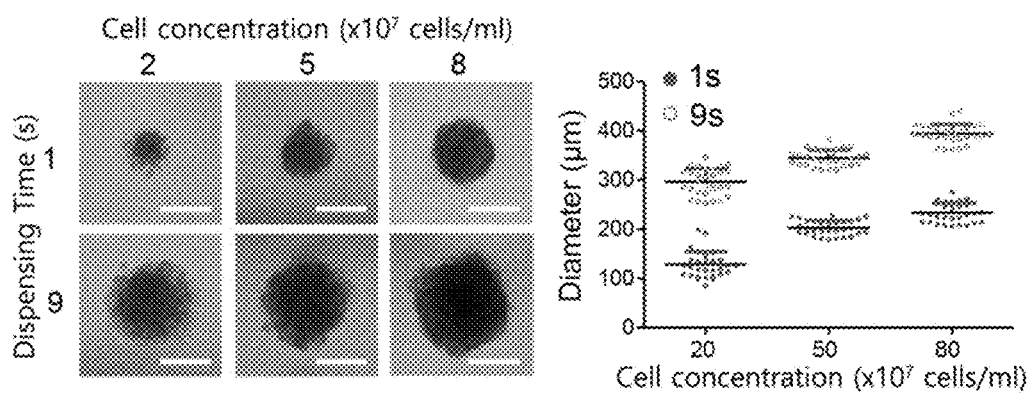
FIG. 5B illustrates cell spheroid sizes dependent upon the concentration of cells included in a second bioink according to an embodiment of the present disclosure.

FIG. 5B illustrates cell spheroid sizes dependent upon the concentration of cells included in a second bioink according to an embodiment of the present disclosure.

Referring to FIG. 5B, it can be confirmed that the size of cell spheroid depends upon the concentration of cells included in the second bioink. The sizes of cell spheroids can be confirmed by increasing the concentrations of cells at a second bioink extrusion time of each of 1 and 9 seconds (scale bar: 200). As a result, it was confirmed that the size of cell spheroid increased with increasing cell concentration at the same extrusion time. In addition, it was confirmed that the size of cell spheroid increased with increasing extrusion time at the same cell concentration. In an embodiment, the diameter of a cell spheroid may be adjusted up to 100 to 400 by controlling a cell extrusion time and a cell concentration.

Figure 6:
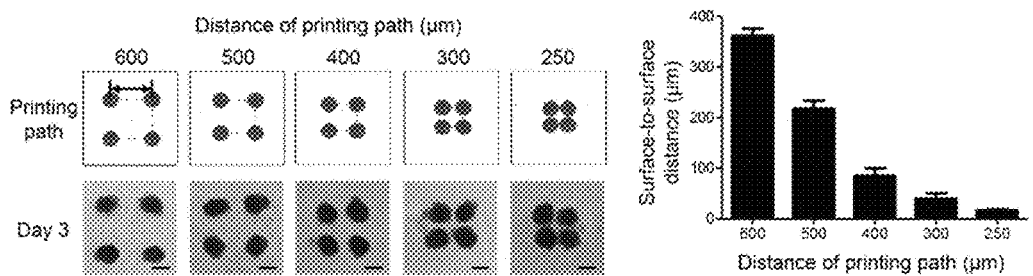
FIG. 6 illustrates a distance between cell spheroids, dependent upon an injection interval of a second bioink according to an embodiment of the present disclosure.

FIG. 6 illustrates a distance between cell spheroids, dependent upon an injection interval of a second bioink according to an embodiment of the present disclosure.

Referring to FIG. 6, the spacing between cell spheroids may be adjusted by controlling a printing path. In this case, the printing path may refer to an extrusion path of the second bioink. It can be confirmed that the spacing between cell spheroids may be determined by adjusting a printing path (scale bar: 200 μm).

In addition, a surface-to-surface distance between cell spheroids formed according to an extrusion spacing of the second bioink can be confirmed from the graph. By adjusting the printing path, the surface-to-surface distance between cell spheroids may be adjusted to a minimum of 20 μm.

FIGS. 7A and 7B illustrate three-dimensional sheet structures formed by patterning cell spheroids according to an embodiment of the present disclosure.

Referring to FIG. 7A, a three-dimensional sheet structure patterned with cell spheroids can be observed. In the three-dimensional sheet structure, empty channels (dotted white lines) through a cell culture medium smoothly passes may be present between grids formed by patterning with the cell spheroids.

Referring to FIG. 7B, three-dimensional sheet structures formed by patterning with cell spheroids formed of multi-type cells can be confirmed (scale bar: 200). The second bioink was mixed with HEK2 and NIH3T3 (fibroblast), thereby manufacturing three-dimensional structures patterned with multi-type cell spheroids.

In addition, various cell types may be mixed with the second bioink to manufacture three-dimensional structures patterned with multi-type cell spheroids.

Figure 7C:
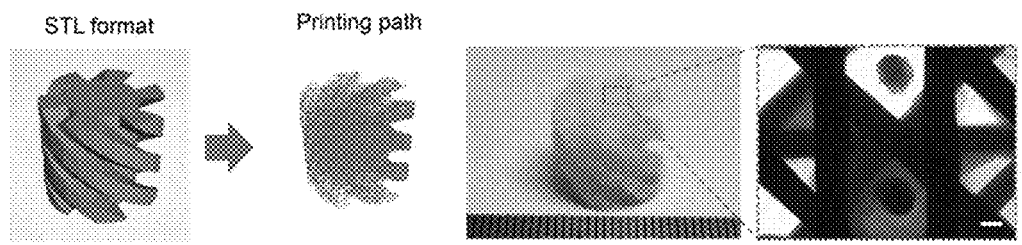
FIG. 7C illustrates a spiral cylindrical structure formed by patterning cell spheroids according to an embodiment of the present disclosure.

FIG. 7C illustrates a spiral cylindrical structure formed by patterning cell spheroids according to an embodiment of the present disclosure.

Referring to FIG. 7C, a spiral cylindrical structure patterned with cell spheroids may be manufactured by adjusting a printing path through design software. After generating a printing path through design software, a matrix and cell extrusion path may be added into the printing path. Accordingly, for example, a spiral cylindrical structure having a diameter of 14.4 mm and a height of 12.4 mm and patterned with cell spheroids may be manufactured (scale bar: 200).

Figure 8:
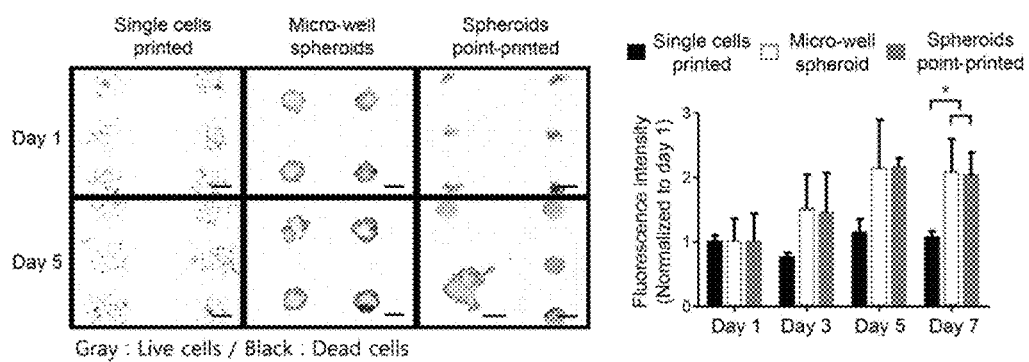
FIG. 8 illustrates cell compatibility analysis results of three-dimensional sheet structures formed by patterning cell spheroids according to an embodiment of the present disclosure.

FIG. 8 illustrates cell compatibility analysis results of three-dimensional sheet structures formed by patterning cell spheroids according to an embodiment of the present disclosure.

Referring to FIG. 8, cell compatibilities of a first group (single cells printed) manufactured by adding dispersed single cells to a matrix and printing the same according to a conventional method, a second group (micro-wells spheroids) including spheroids generated in microwells according to a conventional method, and spheroids manufactured according to the manufacturing process of the present disclosure were compared.

Referring to live and dead assay results, it can be confirmed that the cell spheroids manufactured according to the manufacturing process of the present disclosure exhibit high cell viability, compared to the conventional comparative groups (scale bar: 200). In addition, referring to Alamar blue assay results, it can be confirmed that the cell spheroids manufactured according to the method of the present disclosure exhibit higher metabolic activity than the cell spheroids of the first group and similar metabolic activity to the cell spheroids of the second group.

Figure 9A:
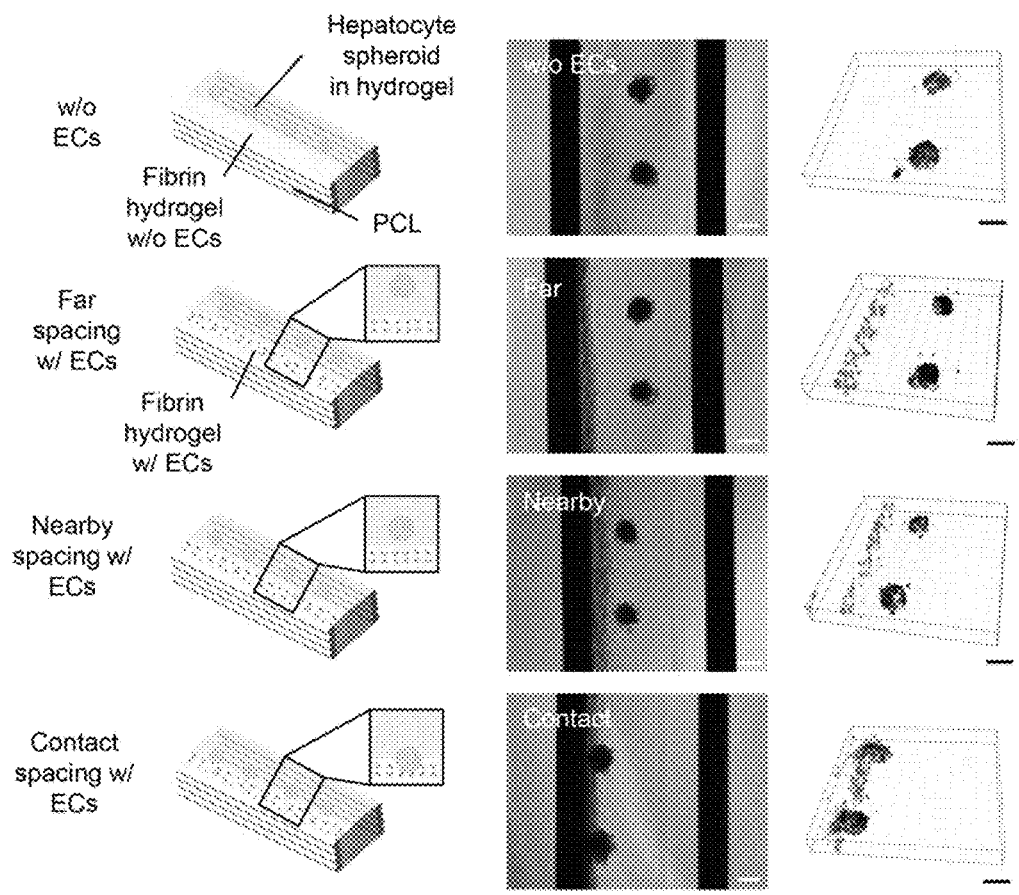
FIG. 9A illustrates structures according to an embodiment of the present disclosure in which a distance between a vascular endothelial cell line pattern and cell spheroids is adjusted.

FIG. 9A illustrates structures according to an embodiment of the present disclosure in which a distance between a vascular endothelial cell line pattern and cell spheroids is adjusted.

Referring to FIG. 9A, a structure wherein a distance between a vascular endothelial cell (HUVEC) line pattern and mouse primary hepatocyte spheroids is adjusted may be manufactured. In this case, a fibrin-based bioink may include vascular endothelial cells, and an endothelial cell line pattern may be printed between PCL.

Through the manufacturing process of the present disclosure, mouse primary hepatocyte spheroids may be patterned to be spaced from a vascular endothelial cell line pattern at a desired interval. Here, a group excluding vascular endothelial cells was called "w/o ECs", a group wherein a distance from mouse primary hepatocyte spheroids to a vascular endothelial cell line pattern was far (e.g., distance on printing path: 500 μm) was called "far", a group wherein a distance from mouse primary hepatocyte spheroids to a vascular endothelial cell line pattern was close (e.g., distance on printing path: 250 μm) was called "Nearby", and a group wherein mouse primary hepatocyte spheroids remained in contact with a vascular endothelial cell line pattern (e.g., distance on printing path: 0 μm) was called "Contacted". Experiments were carried out, and printing results were photographed using a general inverted microscope and a confocal microscope (scale bar: 200 μm).

Figure 9B:
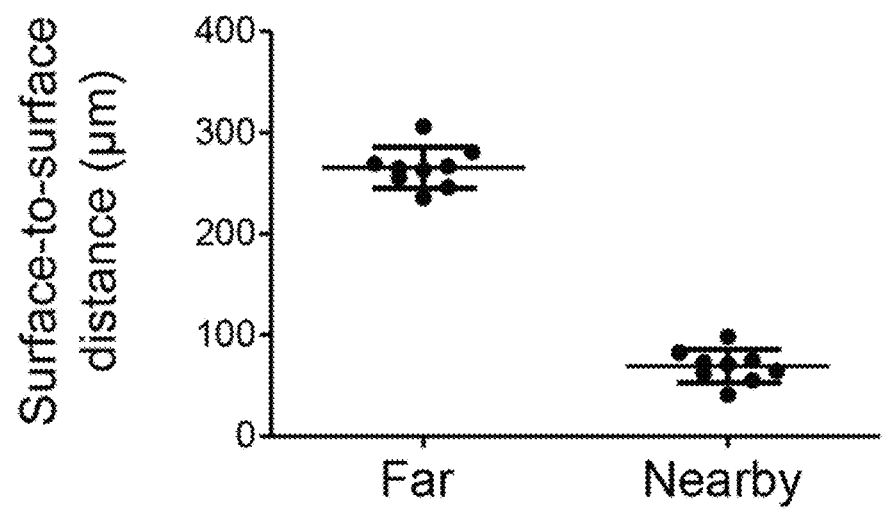
FIG. 9B is a graph illustrating a distance between a vascular endothelial cell line pattern and cell spheroids according to an embodiment of the present disclosure.

In this case, referring to FIG. 9B, a surface-to-surface distance between a vascular endothelial cell line pattern and mouse primary hepatocyte spheroids may be determined from a distance graph between the vascular endothelial cell line pattern and the mouse primary hepatocyte spheroids according to the embodiment of the present disclosure.

Figure 9C:
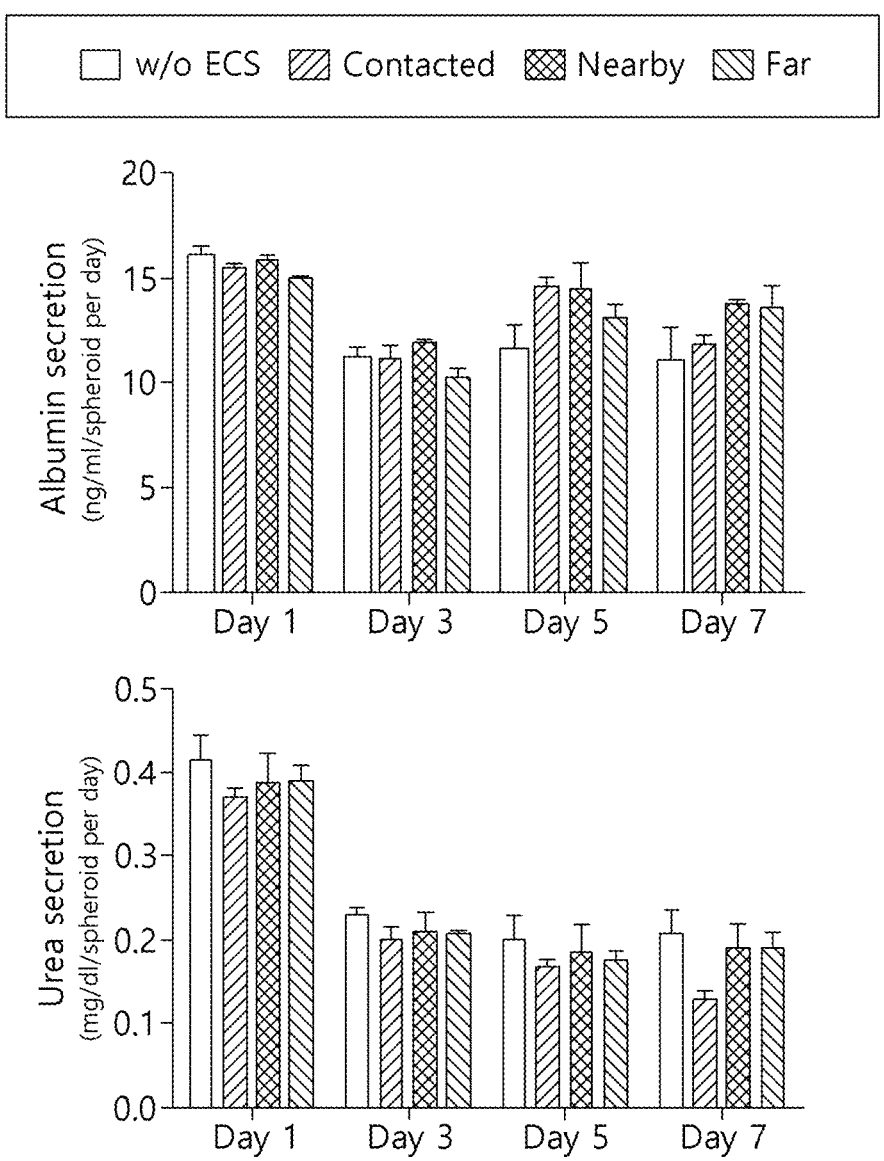
FIG. 9C illustrates comparisons of functions dependent upon a distance between a vascular endothelial cell line pattern and cell spheroids according to an embodiment of the present disclosure.

FIG. 9C illustrates comparisons of functions dependent upon a distance between a vascular endothelial cell line pattern and cell spheroids according to an embodiment of the present disclosure.

Referring to FIG. 9C, albumin and urea secretion amounts dependent upon a distance between a vascular endothelial cell line pattern and mouse primary hepatocyte spheroids were compared. It was confirmed that the albumin and urea secretion amounts depended upon the distance, particularly the albumin and urea secretion amounts of the "Nearby" and "Far" groups were relatively high on day 7 of culture.

As described above, according to an embodiment of the present disclosure, an environment in which cells form spheroids can be provided by spherically extruding a second bioink including dispersed single cells into a matrix of a first bioink and selectively crosslinking only the matrix excluding cells.

In addition, a method of manufacturing cell spheroids according to an embodiment of the present disclosure can be applied to the development of drug test chips for new drug development and artificial tissue mimetics for tissue regeneration. Although the present disclosure has been described through some exemplarily embodiments, various modifications or changes can be made within the scope defined by the following claims, and the technical protection scope of the present disclosure should be defined by the following claims.

DESCRIPTION OF SYMBOLS

201: PCL printing
203: first bioink printing
205: second bioink printing
207: crosslinking
209: dissolving

What is claimed is:
1. A method of manufacturing a cell spheroid, the method comprising:
    extruding a first bioink that is composed of a substrate excluding cells and comprising an alginate;
    forming a spherical space inside the first bioink by extruding a second bioink comprising dispersed cells into the first bioink;
    adding a calcium chloride (CaCl2) solution to the alginate comprised in the first bioink, wherein calcium chloride in the CaCl2 solution is crosslinked with the alginate of the first bioink; and
    dissolving the second bioink, present in the first bioink, in a cell culture medium to form a cell spheroid from the cells of the second bioink.

2. The method according to claim 1, further comprising extruding polycaprolactone (PCL) to form a first PCL structure and a second PCL structure, before the extruding of the first bioink.

3. The method according to claim 2, wherein the extruding of the first bioink comprises:
    forming a matrix of the first bioink, between the first and second PCL structures, by filling the first bioink comprising the alginate between the first and second PCL structures, and
    wherein the forming the spherical space inside the first bioink comprises:
    extruding the second bioink into a position, which is inside the first bioink and is between the first and second PCL structures,
    wherein the crosslinked calcium chloride prevents the second bioink from dispersing when the second bioink is injected into the matrix of the first bioink.

4. The method according to claim 1, wherein, in the extruding of the first bioink, the first bioink comprising the alginate is extruded onto a previously prepared plate.

5. The method according to claim 1, wherein the first bioink comprises hyaluronic acid, gelatin, and the alginate.

6. The method according to claim 1, wherein the second bioink comprises hyaluronic acid, gelatin, calcium chloride, and the cells.

7. The method according to claim 1, wherein, in the extruding of the second bioink, the second bioink is spherically extruded according to at least one of a concentration of gelatin comprised in the first bioink and a concentration of gelatin comprised in the second bioink.

8. The method according to claim 1, wherein the dissolving comprises:
    dissolving hyaluronic acid and gelatin, comprised in the second bioink in the first bioink, in the cell culture medium; and
    culturing the cells, comprised in the second bioink, in the cell culture medium for a predetermined time to form the cell spheroid from the cells.

9. The method according to claim 1, wherein the extruding of the second bioink comprises:
    spherically extruding the second bioink, comprising cells, in the first bioink through a nozzle.

10. The method according to claim 1, wherein a size of the formed cell spheroid is determined according to at least one of an extrusion time and extrusion speed of the second bioink.

11. The method according to claim 1, wherein a size of the formed cell spheroid is determined according to a concentration of cells comprised in the second bioink.

12. The method according to claim 1, wherein the spacing between the formed cell spheroids is determined according to an extrusion path of the second bioink.

13. The method according to claim 1, further comprising removing the alginate of the first bioink to extract the cell spheroid, after the dissolving.

14. The method according to claim 13, further comprising adding an alginate lyase to the first bioink to remove the alginate from the first bioink and extract the cell spheroid.

15. The method according to claim 1, wherein the forming the spherical space inside the first bioink comprises:
    forming the spherical space inside the first bioink by pushing out a part of the first bioink from a portion inside the first bioink by extruding the second bioink having a spherical shape into the portion inside the first bioink.

* * * * *